US010429472B2

(12) United States Patent
Tatebayashi

(10) Patent No.: US 10,429,472 B2
(45) Date of Patent: Oct. 1, 2019

(54) MAGNETIC RESONANCE IMAGING APPARATUS AND METHOD FOR MAGNETIC RESONANCE IMAGING WITH COPYING AND SETTING OF PARAMETER VALUES

(75) Inventor: Isao Tatebayashi, Utsunomiya (JP)

(73) Assignee: TOSHIBA MEDICAL SYSTEMS CORPORATION, Otawara-shi, Tochigi-Ken (JP)

( * ) Notice: Subject to any disclaimer, the term of this patent is extended or adjusted under 35 U.S.C. 154(b) by 1330 days.

(21) Appl. No.: 13/569,619

(22) Filed: Aug. 8, 2012

(65) Prior Publication Data

US 2012/0299592 A1 Nov. 29, 2012

Related U.S. Application Data

(63) Continuation of application No. PCT/JP2011/075177, filed on Nov. 1, 2011.

(30) Foreign Application Priority Data

Nov. 1, 2010 (JP) .................................. 2010-245590

(51) Int. Cl.
*G01R 33/54* (2006.01)
*A61B 5/026* (2006.01)
*A61B 5/055* (2006.01)

(52) U.S. Cl.
CPC ......... *G01R 33/543* (2013.01); *G01R 33/546* (2013.01); *A61B 5/0263* (2013.01); *A61B 5/055* (2013.01)

(58) Field of Classification Search
CPC ............................ G01R 33/543; G01R 33/546
See application file for complete search history.

(56) References Cited

U.S. PATENT DOCUMENTS 6,687,527 B1 * 2/2004 Wu ..................... G01R 33/546
                                                  324/318
7,808,239 B2 * 10/2010 Miyazaki ............. G01R 33/543
                                                  324/309

(Continued)

FOREIGN PATENT DOCUMENTS

JP            03-070547        3/1991
JP          2003-284709        10/2003

(Continued)

OTHER PUBLICATIONS

International Search Report for PCT/JP2011/075177 dated Jan. 24, 2012.

(Continued)

*Primary Examiner* — Dixomara Vargas
(74) *Attorney, Agent, or Firm* — Nixon & Vanderhye P.C.

(57) ABSTRACT

An embodiment of a magnetic resonance imaging apparatus is configured to carry out plural series of imaging while changing plural imaging conditions for a patient on a series basis, and has a storage unit configured to group plural parameter types related to some of the plural imaging conditions for carrying out the series of imaging into a plurality of groups, and to store a parameter value corresponding to one of the parameter types on a group basis, and has a controller which specifies a first series included in the plural series and a group to be used in the first series to read one of the parameter values belonging to the specified group from the storage unit, the controller setting the read parameter value as a parameter value related to some of plural imaging conditions to be used in a second series included in the plural series.

11 Claims, 15 Drawing Sheets

(56) References Cited

U.S. PATENT DOCUMENTS

| | | | |
|---|---|---|---|
| 7,990,140 B2 * | 8/2011 | Sugiura | G01R 33/4828 324/307 |
| 8,080,997 B2 * | 12/2011 | Kassai | G01R 33/56518 324/307 |
| 8,125,222 B2 * | 2/2012 | Sugiura | G01R 33/54 324/307 |
| 8,217,648 B2 * | 7/2012 | Kachi | G01R 33/54 324/307 |
| 8,476,903 B2 * | 7/2013 | Furudate | G01R 33/543 324/307 |
| 8,842,895 B2 * | 9/2014 | Sugiura | A61B 5/0263 382/131 |
| 9,018,953 B2 * | 4/2015 | Umeda | G01R 33/5617 324/309 |
| 2003/0142859 A1 * | 7/2003 | Okuzawa | G06F 19/3406 382/132 |
| 2007/0161889 A1 * | 7/2007 | Mayer | A61B 5/055 600/410 |
| 2009/0175524 A1 | 7/2009 | Kachi et al. | |

FOREIGN PATENT DOCUMENTS

| | | |
|---|---|---|
| JP | 2007-14781 | 1/2007 |
| JP | 2008-302096 | 12/2008 |
| JP | 2009-160273 | 7/2009 |
| WO | WO 2009/151041 | 12/2009 |

OTHER PUBLICATIONS

English Translation of International Preliminary Report on Patentability dated May 14, 2013 for Application No. PCT/JP2011/075177.

Office Action dated May 12, 2015 in JP 2011-239889.

* cited by examiner

EXEMPLARY PARAMETERS GROUPED AND STORED IN PARAMETER STORAGE UNIT

| GROUPING CATEGORY | GROUP | SHORTENED GROUP NAME | PARAMETER TYPE |
|---|---|---|---|
| GROUPING ACCORDING TO PURPOSES | GROUP OF PARAMETER TYPES FOR IDENTIFYING IMAGING PART | PART | OFFSET OF SLICE CENTER, SLICE DIRECTION, PHASE ENCODE DIRECTION, RO DIRECTION, etc. |
| | GROUP OF PARAMETER TYPES FOR IDENTIFYING RESOLUTION | RESOLUTION | SLICE THICKNESS, MATRIX SIZE, FOV, etc. |
| | GROUP OF PARAMETER TYPES FOR OBTAINING VARIOUS VALUES OF CONTRAST | CONTRAST | TR, TE, FLIP ANGLE, etc. |
| GROUPING ACCORDING TO FUNCTIONS | GROUP OF PARAMETER TYPES RELATED TO TimeSLIP | TimeSLIP | TAG AREA, GATE INFORMATION |
| | GROUP OF PARAMETER TYPES RELATED TO MRS | MRS | VOXEL NUMBER, VOXEL SIZE, CONCERNED AREA, etc. |
| | GROUP OF PARAMETER TYPES RELATED TO Tagging | Tagging | Tagging POSITION, etc. |

FIG. 3

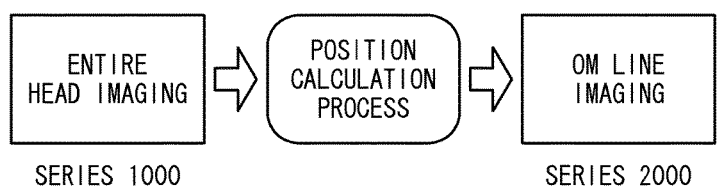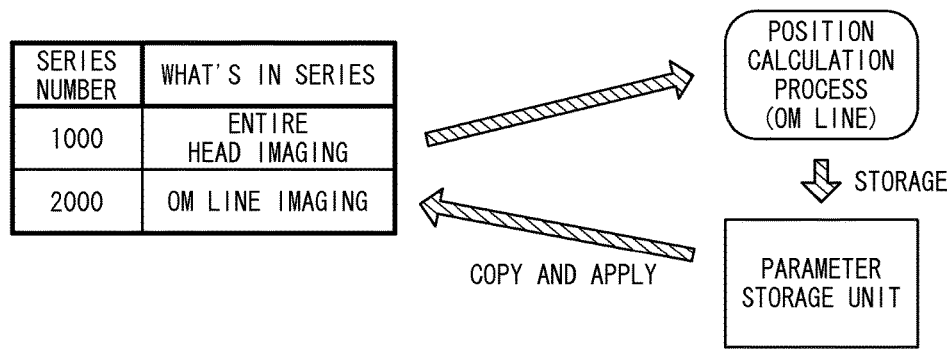
FIG. 11

MAGNETIC RESONANCE IMAGING APPARATUS AND METHOD FOR MAGNETIC RESONANCE IMAGING WITH COPYING AND SETTING OF PARAMETER VALUES

CROSS-REFERENCE TO RELATED APPLICATIONS

This application is a Continuation Application of No. PCT/JP2011/075177, filed on Nov. 1, 2011, and the PCT application is based upon and claims the benefit of priority from Japanese Patent Applications No. 2010-245590 filed on Nov. 1, 2010, the entire contents of which are incorporated herein by reference.

FIELD

An embodiment of the present invention relates to a magnetic resonance imaging apparatus and a method for magnetic resonance imaging.

BACKGROUND

In order that a desired diagnosis image is obtained by the use of a magnetic resonance imaging apparatus, various parameters need to be set to the apparatus in accordance with a purpose of imaging, a use of the diagnosis image and so on, e.g., as disclosed in US 2009/0175524 A1, etc.

Parameters to be set to the apparatus are various, such as parameters related to an imaging target part (e.g., a center position of a slice, a direction of the slice, a direction of phase encoding, etc.), parameters related to image resolution (a thickness of the slice, a size of a matrix, FOV, etc.), parameters related to image contrast (e.g., TR, TE, a flip angle, etc.) and so on.

As is often the case with obtaining an MRI image, e.g., images of a same part of a same patient are taken while contrast is being changed. Although different values have to be set to the parameters related to the contrast each time of imaging in such a case, same values can be copied and set to the parameters related to the imaging target part which do not need to be changed, so that setting time can be shortened and an erroneous setting caused by carelessness can be prevented.

In another case where a treatment history for one and the same patient is diagnosed, an image is taken with a same parameter as that used for imaging in the past so that a comparable image can be obtained more accurately. In such a case as well, the parameters used for imaging in the past are copied and set so that setting time can be shortened and an erroneous setting caused by carelessness can be prevented.

If some or all of the parameters having been set by a user can be copied and used for settings of parameters for a next imaging operation as described above, time required for bothersome parameter settings can be shortened and a risk of an erroneous setting can be reduced.

Although an ordinary magnetic resonance imaging apparatus has such a copy function, its function is limited and is not convenient enough for practical use. According to such an ordinary copy function, e.g., register particular kinds of parameters which can be copied (TR, TE, flip angle, matrix size, etc.) in advance, copy values of the particular parameters having been set and use the copied values for setting parameters for a next imaging operation.

Thus, there are inconveniences such that a value of a parameter desired to be copied cannot be copied unless its kind is registered in advance, and conversely, that a value of a parameter not desired to be copied but registered in advance is automatically copied. Registered kinds of parameters have to be changed in order to solve such inconveniences, but such work takes time by itself and is bothersome.

SUMMARY

Accordingly, a magnetic resonance imaging apparatus and a method for magnetic resonance imaging which provide a copy function convenient for practical use and a function to set parameters efficiently by using the copy function are usually required.

An embodiment of a magnetic resonance imaging apparatus is configured to carry out a plurality of series of imaging while changing a plurality of imaging conditions for a patient on a series basis, and has a parameter storage unit configured to group a plurality of parameter types related to some of the plural imaging conditions for carrying out the series of imaging into a plurality of groups, the parameter storage unit configured to store a parameter value corresponding to one of the parameter types on a group basis, and has a controller configured to specify a first series included in the plural series and a group to be used in the first series so as to read one of the parameter values belonging to the specified group from the parameter storage unit, the controller being configured to set the read parameter value as a parameter value related to some of a plurality of imaging conditions to be used in a second series included in the plural series.

BRIEF DESCRIPTION OF DRAWINGS

FIG. 3 illustrates exemplary parameters grouped and stored in a parameter storage unit;

FIG. 11 is a second exemplary diagram which illustrates an idea of an operation to copy and apply parameters from post-process data;

DESCRIPTION OF EMBODIMENTS

An embodiment of the magnetic resonance imaging apparatus will be explained hereafter with reference to the drawings.

(Constitution)

Figure 1:
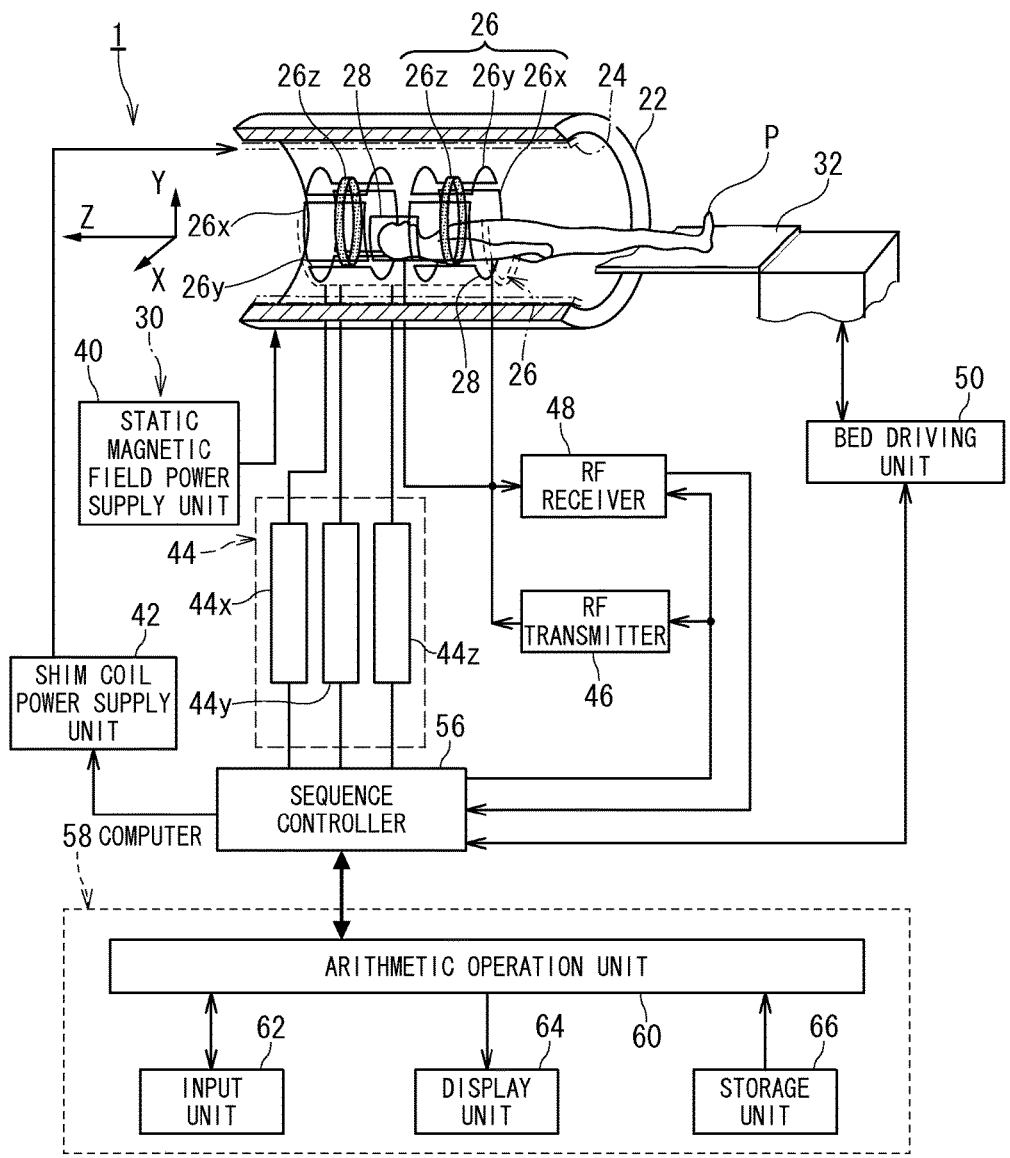
FIG. 1 is a first diagram which depicts an exemplary constitution of a magnetic resonance imaging apparatus of an embodiment.

FIG. 1 is a block diagram which depicts an exemplary constitution of a magnetic resonance imaging apparatus 1. The magnetic resonance imaging apparatus 1 has a cylindrical static field magnet 22 which forms a static magnetic field, a cylindrical shim coil 24 provided coaxially with and inside the static field magnet 22, a gradient coil 26, an RF coil 28, a control unit 30 and a bed 32 on which a test object (a patient) P can be mounted.

An exemplary coordinate system of the apparatus including X-, Y- and Z-axes which are perpendicular to one another is defined here, as follows. To begin with, suppose that the static field magnet 22 and the shim coil 24 are arranged in such a way that their axial directions cross perpendicularly to the vertical direction, and that the axial directions of the static field magnet 22 and the shim coil 24 are in the direction of the Z-axis. Suppose further that the vertical direction is the direction of the Y-axis, and that the bed 32 is arranged in such a way that the direction normal to a top mounting plate of the bed 32 is in the direction of the Y-axis.

The control unit 30 has a static magnetic field power supply unit 40, a shim coil power supply unit 42, a gradient magnetic field power supply unit 44, an RF transmitter 46, an RF receiver 48, a bed driving unit 50, a sequence controller 56 and a computer 58.

The gradient magnetic field power supply unit 44 is formed by an X-axis gradient magnetic field power supply unit 44x, a Y-axis gradient magnetic field power supply unit 44y and a Z-axis gradient magnetic field power supply unit 44z. Further, the computer 58 is formed by an arithmetic operation unit 60, an input unit 62, a display unit 64 and a storage unit 66.

The static field magnet 22 is connected to the static magnetic field power supply unit 40, and forms a static magnetic field in imaging space by means of an electric current supplied by the static magnetic field power supply unit 40. The shim coil 24 is connected to the shim coil power supply unit 42, and levels the static magnetic field off by means of an electric current supplied by the shim coil power supply unit 42. The static field magnet 22 is formed by a superconductive coil in lots of cases. The static field magnet 22 is connected to the static magnetic field power supply unit 40 in time of excitation, and is usually disconnected once having been excited. Incidentally, the static field magnet 22 may be formed by a permanent magnet without being provided with the static magnetic field power supply unit 40.

The gradient coil 26 has an X-axis gradient coil 26x, a Y-axis gradient coil 26y and a Z-axis gradient coil 26z. The gradient coil 26 is shaped like a cylinder inside the static field magnet 22. The X-, Y- and Z-axis gradient coils 26x, 26y and 26z are connected to the X-, Y- and Z-axis gradient magnetic field power supply units 44x, 44y and 44z, respectively.

The X-, Y- and Z-axis gradient magnetic field power supply units 44x, 44y and 44z each provide the X-, Y- and Z-axis gradient coils 26x, 26y and 26z with an electric current, respectively, so that gradient magnetic fields Gx, Gy and Gz are each formed in the directions of the X-, Y- and Z-axes in the imaging space, respectively.

The gradient magnetic fields Gx, Gy and Gz in three directions in the device coordinate system are combined, so that logical axes which are a slice direction gradient magnetic field Gss, a phase encode direction gradient magnetic field Gpe and a read out direction (frequency encode direction) gradient magnetic field Gro each can be set in any direction. The static magnetic field is overlaid with each of the gradient magnetic fields in the slice, phase encode and read out directions.

The RF transmitter 46 generates an RF pulse having a Larmor frequency for producing a nuclear magnetic resonance on the basis of control information provided by the sequence controller 56, and transmits the RF pulse to the RF coil 28 for transmission. The RF coil 28 may be a whole body coil (WBC) for transmitting and receiving an RF pulse contained in a gantry, or a local coil for receiving an RF pulse provided close to the bed 32 or the test object P. The RF coil 28 for transmission receives an RF pulse from the RF transmitter 46 and transmits the RF pulse to the test object P. Meanwhile, the RF coil 28 for receiving receives an MR signal (radio frequency signal) produced as a result of a nuclear spin excited by the RF pulse inside the test object P. The MR signal is detected by the RF receiver 48.

The RF receiver 48 carries out various data processing such as pre-amplification, intermediate frequency conversion, phase detection, baseband frequency amplification, filtering and so on for the detected MR signal, and then A/D (analog to digital)-converts the MR signal so as to generate raw data which is digitized complex data. The RF receiver 48 outputs the produced raw data of the MR signal to the sequence controller 56.

The arithmetic operation unit 60 controls the entire magnetic resonance imaging apparatus 1 as a system, which will be explained by the use of a drawing referred to later.

The sequence controller 56 stores therein control information necessary for driving the gradient magnetic field power supply unit 44, the RF transmitter 46 and the RF receiver 48 as instructed by the arithmetic operation unit 60. The control information mentioned here is, e.g., sequence information such that operation control information related to strength, a period of application or timing of application of a pulse current to be applied to the gradient magnetic field power supply unit 44 is written.

The sequence controller 56 drives the gradient magnetic field power supply unit 44, the RF transmitter 46 and the RF receiver 48 in accordance with a stored particular sequence so as to generate the gradient magnetic fields on the X-, Y- and Z-axes Gx, Gy and Gz, respectively, and an RF pulse. Further, the sequence controller 56 receives raw data of an MR signal provided by the RF receiver 48, and provides the arithmetic operation unit 60 with the received raw data of the MR signal.

Figure 2:
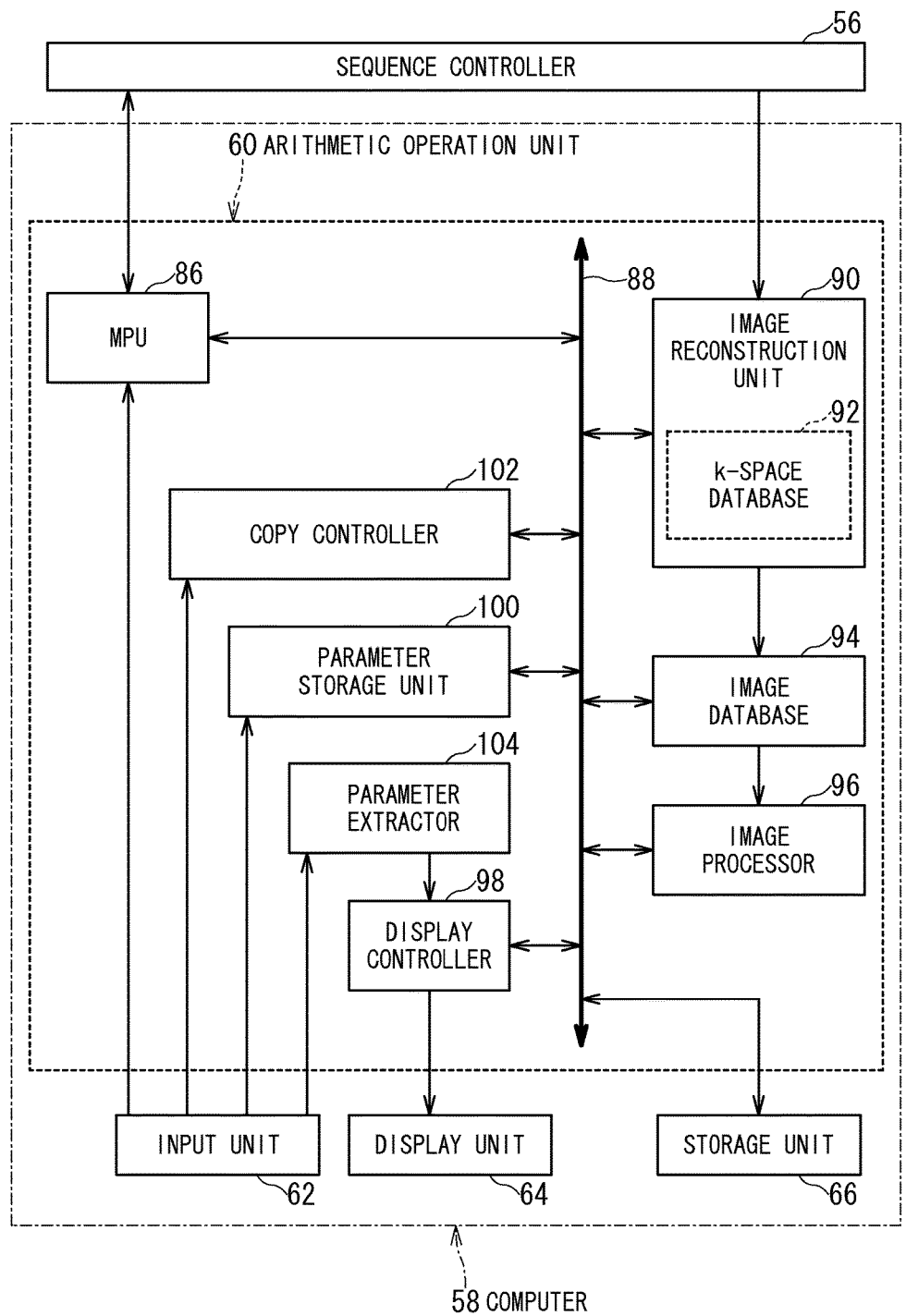
FIG. 2 is a second diagram which depicts the exemplary constitution of the magnetic resonance imaging apparatus of the embodiment.

FIG. 2 is a functional block diagram of the computer 58 depicted in FIG. 1. As depicted in FIG. 2, the arithmetic operation unit 60 of the computer 58 has an MPU (Micro Processor Unit) 86, a system bus 88, an image reconstruction unit 90, an image database 94, an image processor 96, a display controller 98, a parameter storage unit 100, a copy controller 102 and a parameter extractor 104.

The MPU 86 controls the MRI apparatus 1 entirely as a system through lines including the system bus 88 for setting imaging conditions, an imaging operation and displaying an image after the imaging operation. Further, the MPU 86 works as a unit for setting imaging conditions, sets imaging conditions including a pulse sequence on the basis of various kinds of parameters directly provided from the input unit 62 or parameters for imaging set by functions described later of the copy controller 102, the parameter storage unit 100 and the parameter extractor 104, and provides the sequence controller 56 with the imaging conditions having been set.

The image reconstruction unit 90 contains a k-space database 92. The image reconstruction unit 90 arranges the raw data of the MR signal provided from the sequence controller 56 in k-space formed in the k-space database 92 as k-space data. Further, the image reconstruction unit 90 carries out an image reconstruction process including two-dimensional Fourier transformation for the k-space data, so as to generate image data of every slice of the test object P. The image reconstruction unit 90 preserves the generated image data in the image database 94.

The image processor 96 takes in image data from the image database 94, carries out particular image processing for the image data and stores the image data having been image-processed in the storage unit 66 as image data to be displayed.

The display controller 98 does control operations for displaying a screen on which imaging conditions including a function to copy parameters for imaging can be set and a screen on which image processing conditions can be set as a user interface, as controlled by the MPU 86. Besides, the display controller 98 does a control operation for displaying an image to be displayed having been image-processed on the display unit 64. The display unit 64 is formed by including, e.g., a liquid crystal panel, etc. The display unit 64 displays various kinds of setting screens and images to be displayed as controlled by the display controller 98.

The input unit 62 is formed by including, e.g., a keyboard, a mouse, etc. The input unit 62 provides a user with a function to set imaging conditions and image processing conditions. Further, the storage unit 66 stores therein a program to be run by the MPU 86 and various kinds of data.

The parameter storage unit 100 classifies types of parameters related to the imaging conditions into a plurality of groups. The parameter storage unit 100 stores therein parameter values having been set and corresponding to the types of parameters in connection with the classified groups.

Further, the copy controller 102 specifies one of the groups so as to read a parameter value having been set and belonging to the specified group from the storage unit 100. The copy controller 102 does control operations such as to copy and apply a parameter value having been read as a parameter value belonging to the corresponding same group and included in parameters of new imaging conditions to be set.

Suppose that a plurality of series of images is taken while imaging conditions for a patient is being changed for each of the series on the basis of a scenario corresponding to a test purpose. The parameter extractor 104 extracts a group of parameter values to be set in common to all or part of the plural series of images to be taken in accordance with the scenario. The parameter values of the extracted group are stored in the parameter storage unit 100 on a group basis.

Then, the parameter values stored in the parameter storage unit 100 are displayed, via the display controller 98, on the display unit 64 as necessary.

Functions of the parameter storage unit 100, the copy controller 102 and the parameter extractor 104 will be specifically explained below.

(Function to Copy Parameters)

FIG. 3 illustrates exemplary parameter types grouped and stored in the parameter storage unit 100. There are various parameters for imaging to be set to the magnetic resonance imaging apparatus 1. There are several conceivable grouping categories. The embodiment employs, e.g., grouping according to purposes and grouping according to functions.

The groups according to purposes include 1) a group of parameter types for identifying an imaging part (shortened as "part"), 2) a group of parameter types for identifying resolution (shortened as "resolution"), 3) a group of parameter types for obtaining various values of contrast (shortened as "contrast"), etc.

The parameter types belonging to the "position" group include an offset of the slice center (distance between the slice center and the center of the magnetic field), a slice direction, a phase encode (PE) direction, an RO (Read Out) direction, etc. Set these parameter values so as to specify an imaging part.

The parameter types belonging to the "resolution" group include a slice thickness, a matrix size, FOV (Field Of View), etc. Set these parameter values so as to specify resolution of an image.

The parameter types belonging to the "contrast" group include TR (repetition interval), TE (echo time), a flip angle, etc. Set these parameter values properly so as to take images of respective organizations in the imaging part with different contrast values.

Meanwhile, the groups according to functions include groups based on methods for imaging each having a particular function such as TimeSLIP, MRS or Tagging. Parameter types belonging to each of the groups according to functions are specific to the relevant group. Parameter types including a tag area belong to the "TimeSLIP" group. Parameter types including a voxel number and a voxel size belong to the "MRS" group. Parameter types including a Tagging position belong to the "Tagging" group.

The grouping categories or specific kinds or members of the groups are not limited to the above examples, and can be different ones. There are, e.g., a category for grouping imaging parameters in time of imaging in the past according to imaging date and time, or a category for grouping parameters calculated from data obtained by means of some post-process carried out on imaging data.

Incidentally, the parameter types belonging to the respective groups can be repeated among the groups.

The magnetic resonance imaging apparatus 1 of the embodiment has functions to group parameter values having been set in a certain case of imaging or obtained from post-processed data, to store the grouped parameter values in the parameter storage unit 100, and to copy the stored parameters on a group basis so as to apply the copied parameters to parameter settings in another case of imaging. That function will further be explained more specifically.

(1) Case 1: Copy and Apply Parameters Having been Set in a Certain Series

It is generally known in the field of medical image diagnosis that a diagnosis or diagnosis image is managed in layers which are "patient", "study", "series" and "image" from top to bottom. The lowest "image" layer implies each of the images. The "series" layer can include a plurality of the "images". Further, the "study" layer can include a plurality of the "series".

Figure 4:
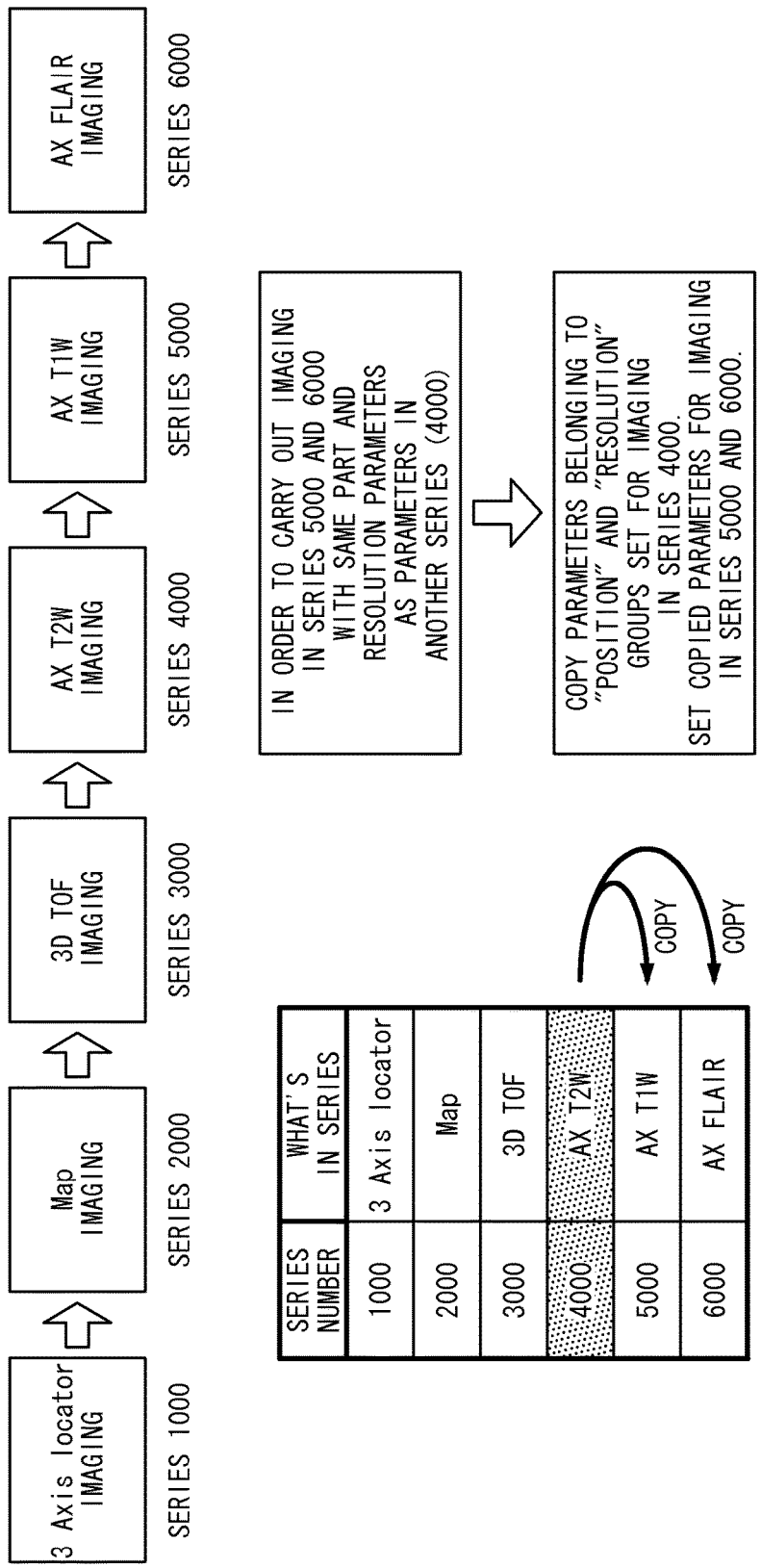
FIG. 4 is a first exemplary diagram which illustrates an idea of an operation to copy and apply parameters in another series.

FIG. 4 illustrates an exemplary flow of an imaging study of the head. According to this example, one imaging study of the head includes six series which are series 1000 through 6000. In the series 1000, e.g., take one image for positioning in each of X-, Y- and Z-directions. In the series 2000, take a map image for a purpose of adjusting evenness of the magnetic field, etc. In the series 3000, carry out three-dimensional TOF (Time Of Flight) imaging so as to take an image of a blood flow in the head. In the series 4000 and 5000, specify a particular imaging surface (e.g., particular axial surface) and carry out T2-weighted imaging and T1-weighted imaging for the imaging surface, respectively. Further, carry out FLAIR (FLuid Attenuated Inversion Recovery) imaging which attenuates cerebrospinal fluid for the same imaging surface in the series 6000.

In the three series 4000 through 6000, take images of the same imaging surface of the head with different contrast values. Thus, it is necessary in those three series to set a same value to each of the parameters belonging to the "part" group. Further, it is necessary to set a same value to each of the parameters belonging to the "resolution" group in order to observe images in the three series with a same resolution value.

Thus, the parameters set in the series 4000 belonging to the "part" or "resolution" group can be easily copied on a group basis according to the embodiment.

Figure 5:
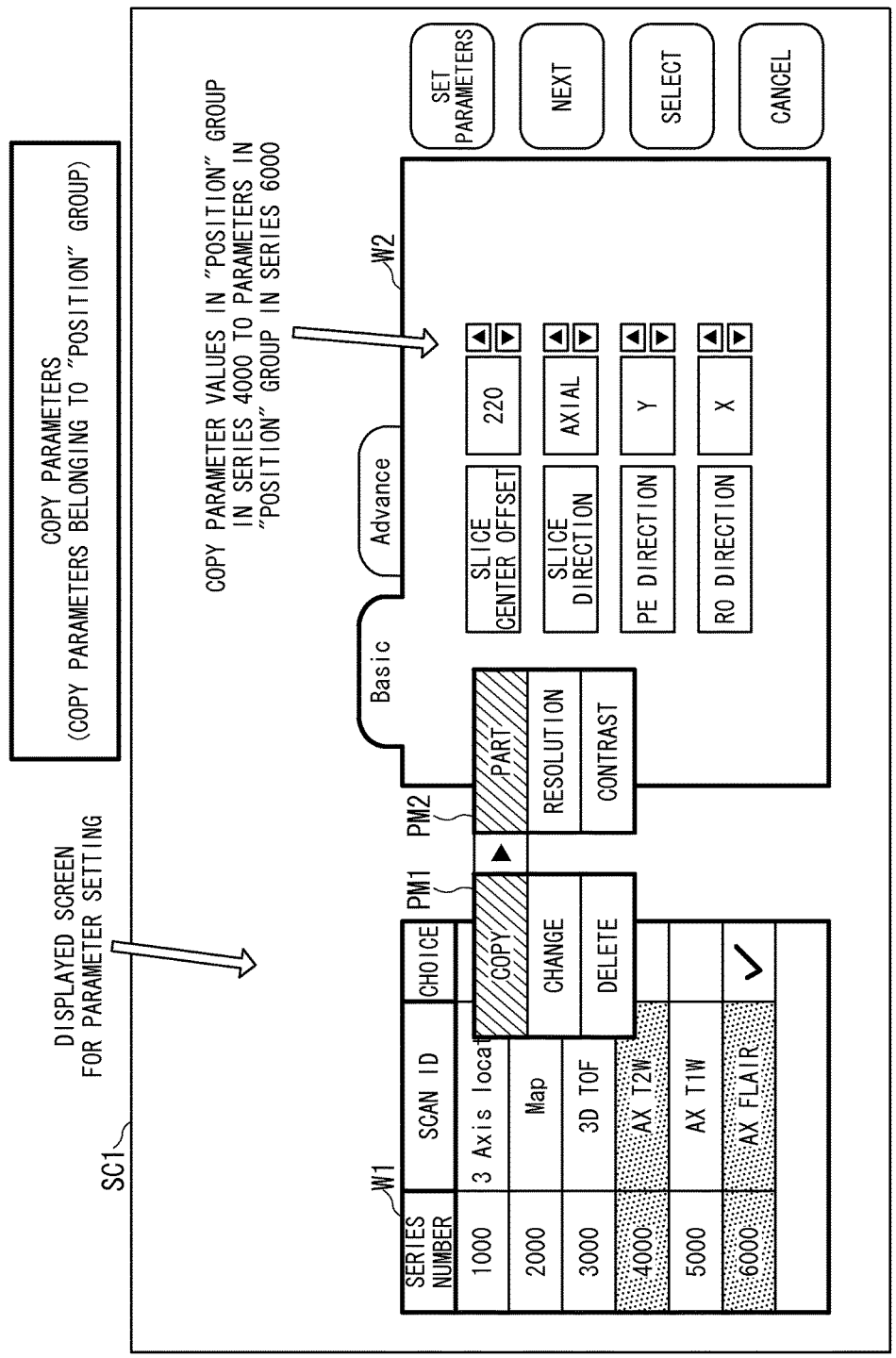
FIG. 5 is a first diagram which illustrates an exemplary operation screen to be used when parameters in another series are copied and applied.

FIG. 5 illustrates an exemplary parameter setting screen SC1 having a copy function. This screen is displayed on the display unit 64 of the magnetic resonance imaging apparatus 1.

On left hand and right hand sides of the parameter setting screen SC1, a series display window W1 and a parameter setting window W2 are displayed, respectively. On the series display window W1, numbers and content of the "series" included in the corresponding "study" are displayed. On the series display window W1 in FIG. 5, the respective series corresponding to the "imaging study of the head" depicted in FIG. 4. The series display window W1 is provided with a "choice" column on the right end. Click a box in the "choice" column with a mouse or something so that one of the series is chosen and the box of the chosen series is checked. The series 6000, e.g., is chosen in FIG. 5, which indicates that a user is about to set various parameters related to imaging in the series 6000.

Then, choose a "series" (first series) and a group of a copy source. Shift a cursor, e.g., onto the position of the series 4000 and right-click, so that a pop-up menu PM1 appears and the series 4000 is chosen as the series of the copy source. Then, shift the cursor onto the position of "copy" in the pop-up menu PM1, so that a pop-up menu PM2 for choosing a group further appears next to the pop-up menu PM1. The groups which are, e.g., "part", "resolution" and "contrast" are indicated on the pop-up menu PM2. Then, shift the cursor onto "part" and click, so that the parameter types and parameter values belonging to the "part" group in the parameters having been set in the series 4000 being the copy source appear on the parameter setting window W2. The user checks the indicated parameter values and clicks a "select" button placed on the right of the parameter setting window W2. Owing to the click, the parameter values in the "part" group having been set in the series 4000 (first series) are collectively copied and set as parameter values in the "part" group in the series 6000 (second series).

Figure 6:
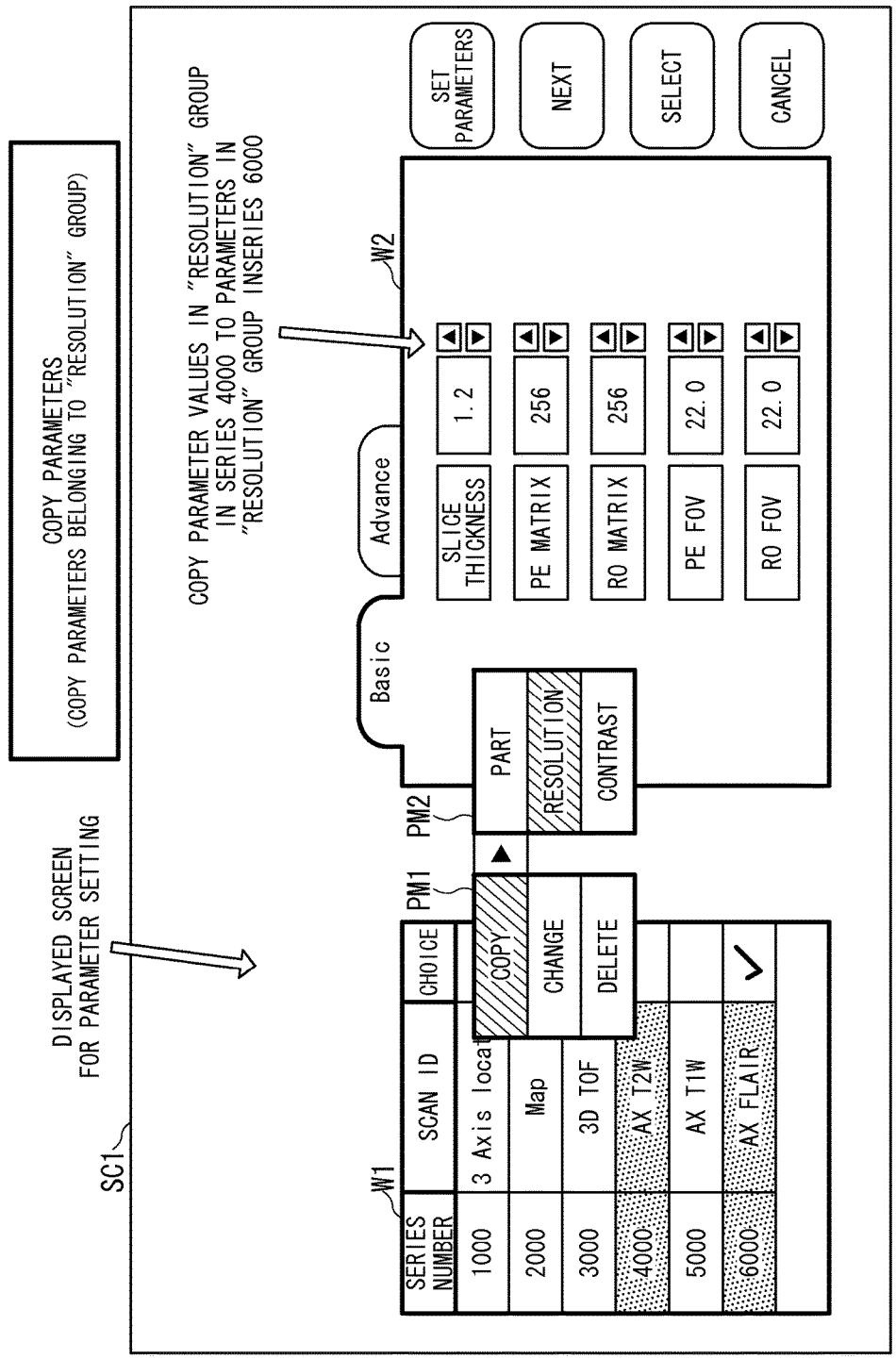
FIG. 6 is a second diagram which illustrates an exemplary operation screen to be used when parameters in another series are copied and applied.

FIG. 6 illustrates an exemplary case where the parameter values belonging to the "resolution" group are copied by means of exactly the same operation. Choose "resolution" and click after the pop-up menu PM2 appears, so that the types and values of the parameters included in the parameters having been set in the series 4000 being the copy source which belong to the "resolution" group appear on the parameter setting window W2. Then, click the "select" button so that the parameter values in the "resolution" group having been set in the series 4000 are collectively copied and set as parameter values in the "position" group in the series 6000.

Group the parameter types as described above, so that the parameters related to the "part" or "resolution" desired to be copied can be collectively and easily copied.

Meanwhile, the imaging method in the series 6000 is a FLAIR method which uses contrast-related parameters being different from those used for the T2-weighted imaging carried out in the series 4000. Thus, the contrast-related parameters used in the series 4000 copied into the series 6000 would cause inconvenience as an opposite effect. According to the embodiment, merely avoid choosing the "contrast" group as an object to be copied so as to keep the contrast-related parameters from being copied, so that inconvenient copies can be easily avoided.

Incidentally, if a parameter value indicated in the pop-up menu PM2 as an object to be copied needs to be changed, change the parameter value before clicking the "select" button and then click the "select" button.

Figure 7:
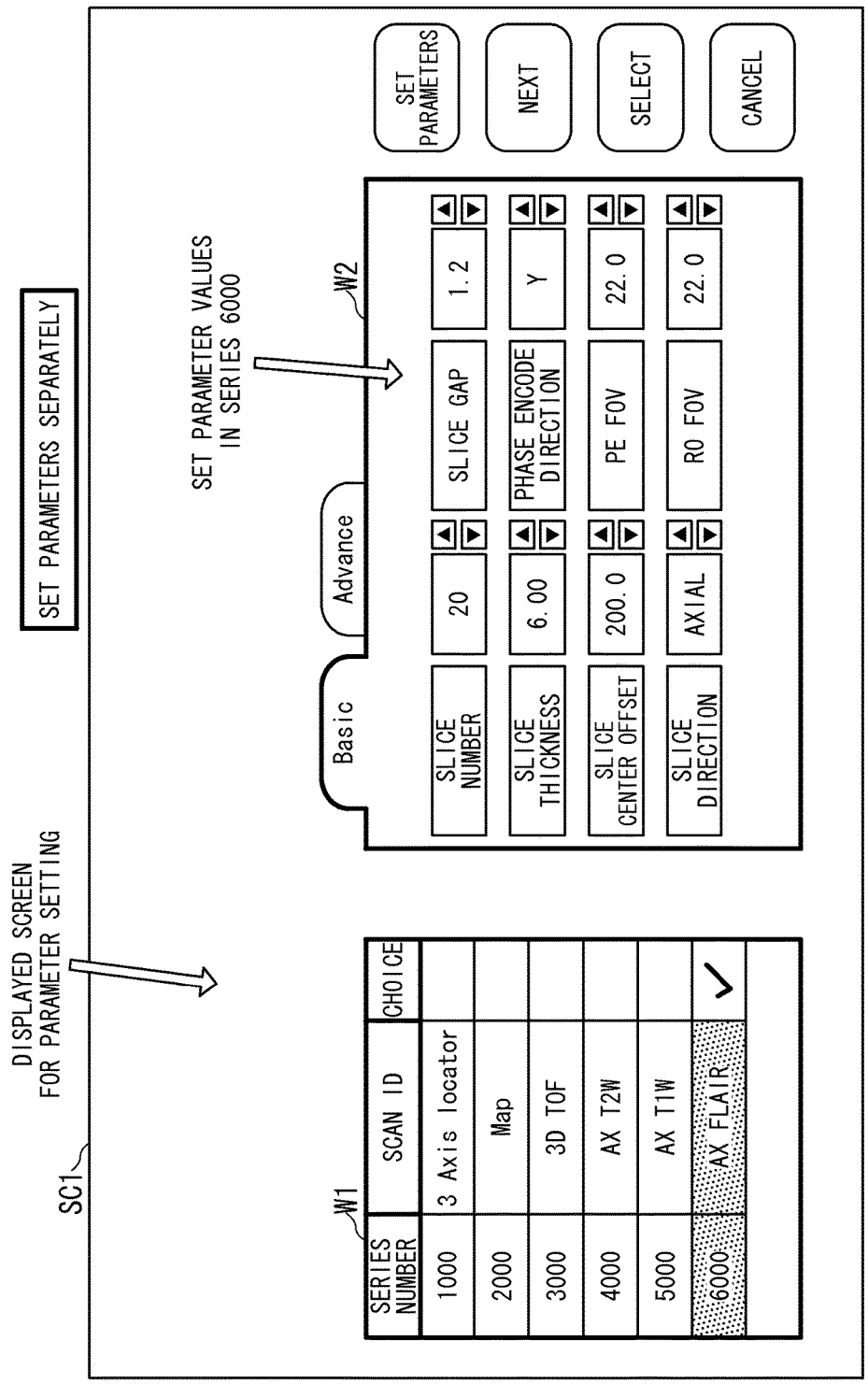
FIG. 7 illustrates an exemplary operation screen to be used when parameters are separately set.

Further, parameters can be separately set as usual without the use of the copy function. If that is the case, choose a series in which parameters are desired to be set (choose the series 6000 in FIG. 7) so that the parameters to be set in the series 6000 appear on the parameter setting window W2 as depicted in FIG. 7. The respective parameter values can be separately set at this phase.

Figure 8:
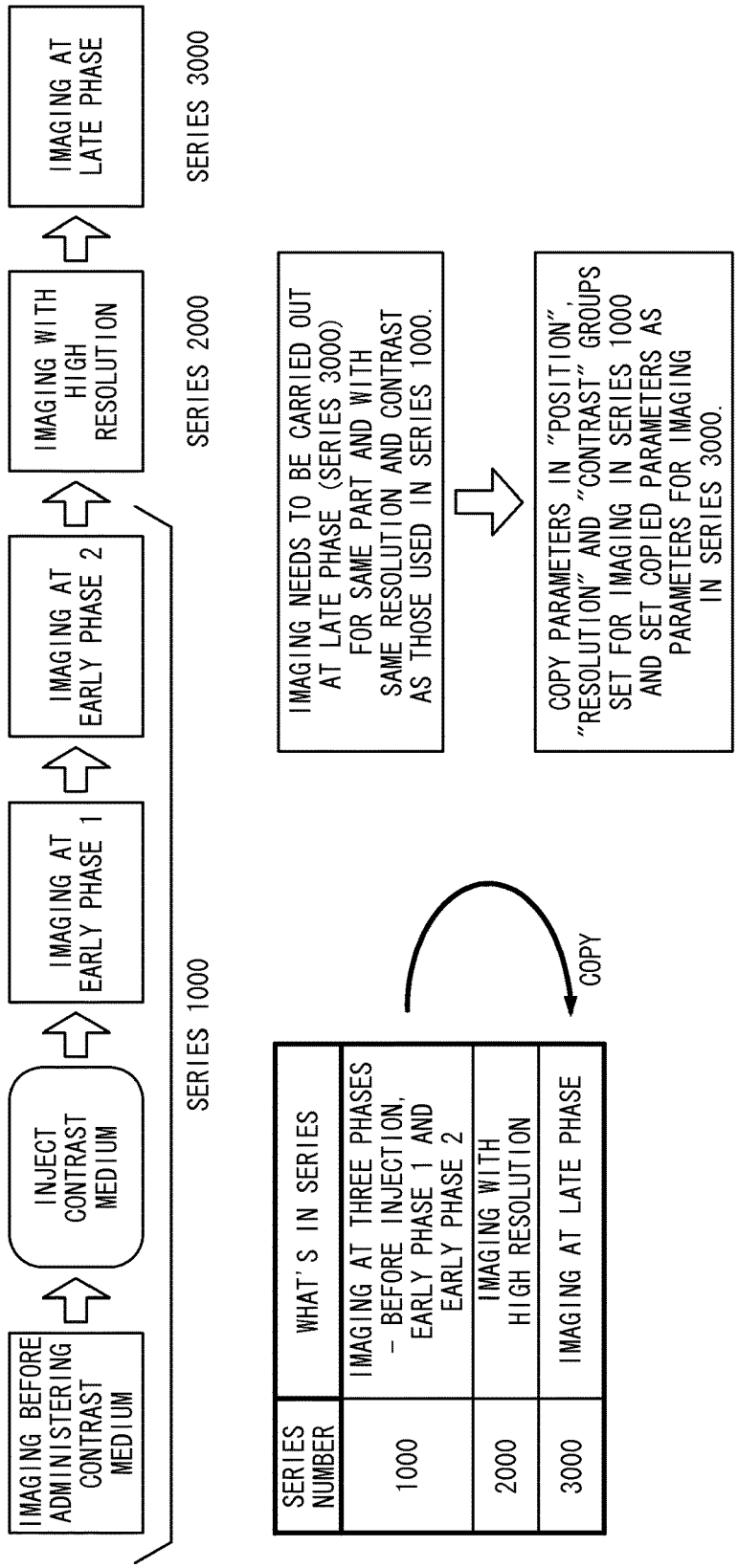
FIG. 8 is a second exemplary diagram which illustrates an idea of an operation to copy and apply parameters in another series.

FIG. 8 illustrates another exemplary study in which parameters are copied and applied between different series, which is a "contrast dynamic imaging study". In a contrast dynamic imaging study, carry out imaging plural times before injecting a contrast medium and in a particular period of time after the injection (e.g., early phase 1, early phase 2 and late phase) in lots of cases. In FIG. 8, e.g., carry out imaging in the series 1000 three times, i.e., before the contrast medium is injected, and at the early phase 1 and the early phase 2 after the injection. One and the same imaging part is made an object for which imaging is carried out plural times with one and the same resolution and contrast in the series 1000 as usual. Then, after carrying out imaging with high resolution in the series 2000, carry out late phase imaging in the series 3000. It is preferable to carry out the late phase imaging for the same imaging part in the same condition as those in the series 1000 from a viewpoint of comparison.

Thus, make use of the function to copy parameters between different series in the "contrast dynamic imaging study" as well, and set the same imaging conditions (all parameters except for the number of times of imaging and when imaging starts) as those set to the imaging in the series 1000 (first series) as imaging conditions in the series 3000 (second series). Copy, e.g., the parameters belonging to each of the "part", "resolution" and "contrast" groups having been set to the imaging in the series 1000 collectively, so as to apply the copied parameters to parameter settings in the "part", "resolution" and "contrast" groups in the series 3000. The parameter settings can be resultantly carried out quickly and accurately without an error in the series 3000.

In addition, it is conceivable to gather parameters "except for" specified particular parameters to form one group, and to collectively copy the parameters "except for" the specified particular parameters. The number of parameters set to the magnetic resonance imaging apparatus 1 is as large as up to several hundred as usual. Thus, specify particular parameters not to be copied instead of specifying the parameters to be copied, and copy the parameters except for the specified ones collectively, so that the parameters can be efficiently set without an error.

Figure 9:
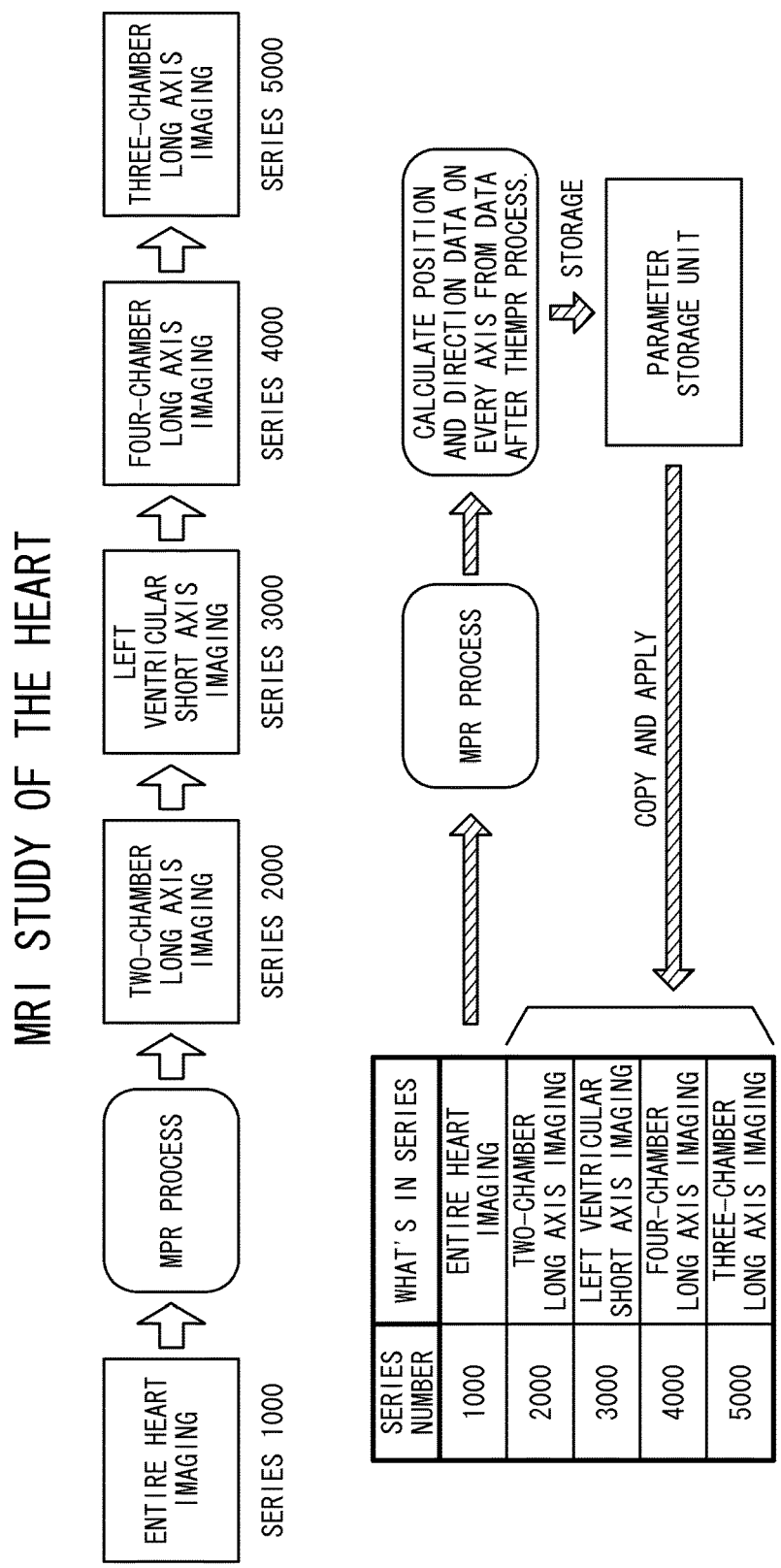
FIG. 9 is a first exemplary diagram which illustrates an idea of an operation to copy and apply parameters from post-process data.

(2) Case 2: Copy and Apply Parameters Obtained in Post-Process to Different Imaging FIG. 9 illustrates an exemplary MRI study of the heart. As is often the case with the MRI study of the heart, take a sliced image of a particular section of the heart such as a two-chamber long axis image, a left ventricular short axis image, a four-chamber long axis image and a three-chamber long axis image in addition to taking an image of the entire heart. According to the embodiment, carry out a post-process such as an MPR process on imaging data (3D data) of the entire heart. Calculate a slice position and direction data corresponding to a desired section from the post-process data after the MPR process. Group, for every section, the slice position and direction data of each of the sections and store them in the parameter storage unit 100. Then, copy and apply parameters related to the relevant slice position and slice direction stored in the parameter storage unit 100 and, in addition, synchronization condition such as an R-R interval having different values patient by patient in order to take a two-chamber long axis image (series 2000) and to take images in the successive series.

Figure 10:
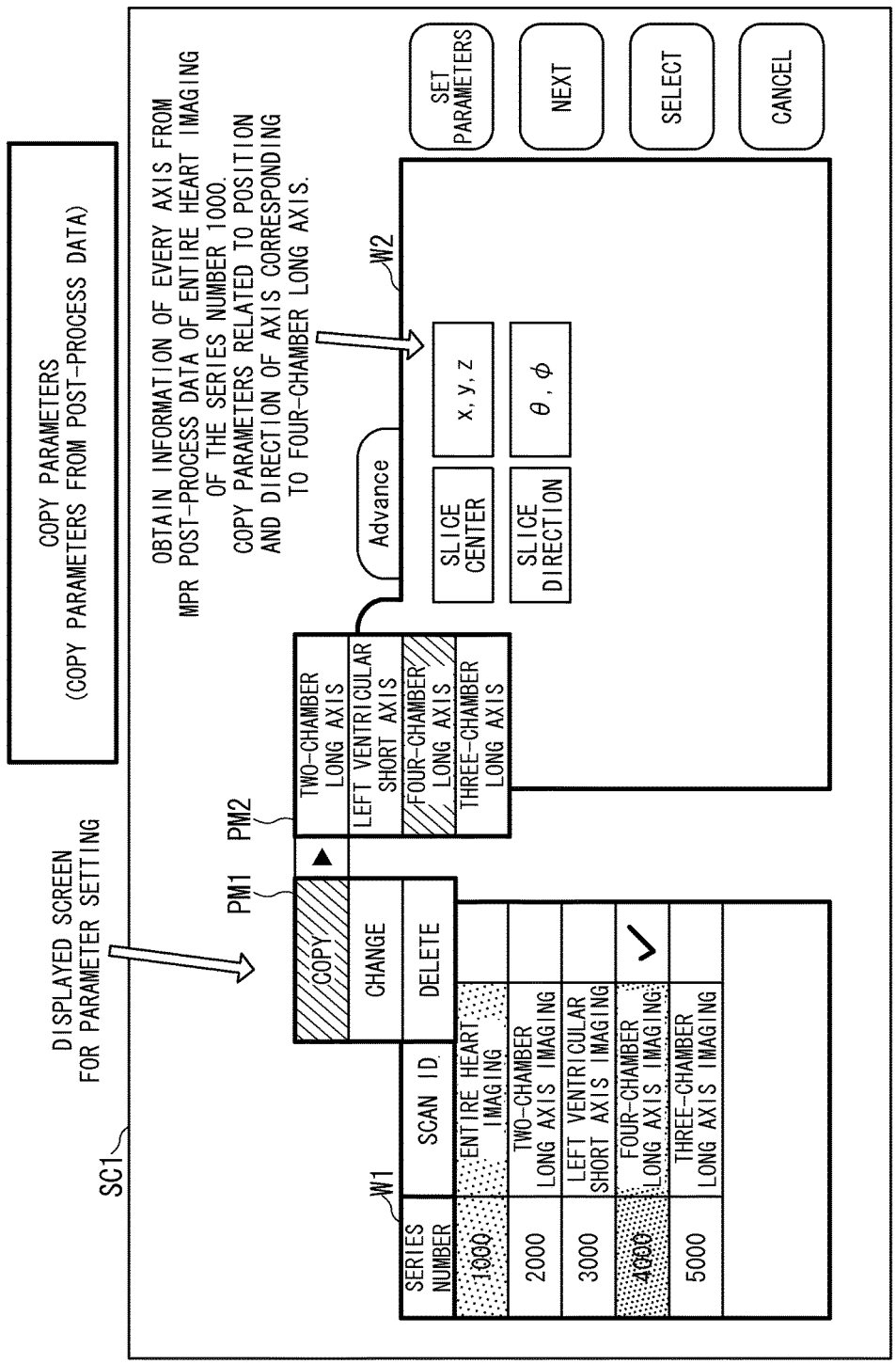
FIG. 10 is a first diagram which illustrates an exemplary operation screen to be used when the parameters are copied and applied from the post-process data.

A method for copying and applying desired parameters is similar to the previously described method. As illustrated in FIG. 10, e.g., choose a series to be set (four-chamber long axis imaging in the series 4000), and then right-click "entire heart imaging" in the series 1000 (first series) so as to specify a "four-chamber long axis" group. Then, parameters in the "four-chamber long axis" group included in the parameters stored in the copy controller 102 are copied and set as parameters for "four-chamber long axis imaging" in the series 4000 (second series).

Copy and apply the post-process data after the MPR process, etc. so as to quickly and accurately set parameters of a position and a direction of a desired section. Further, copy synchronization condition such as the R-R interval so as to set more accurate conditions.

Figure 12:
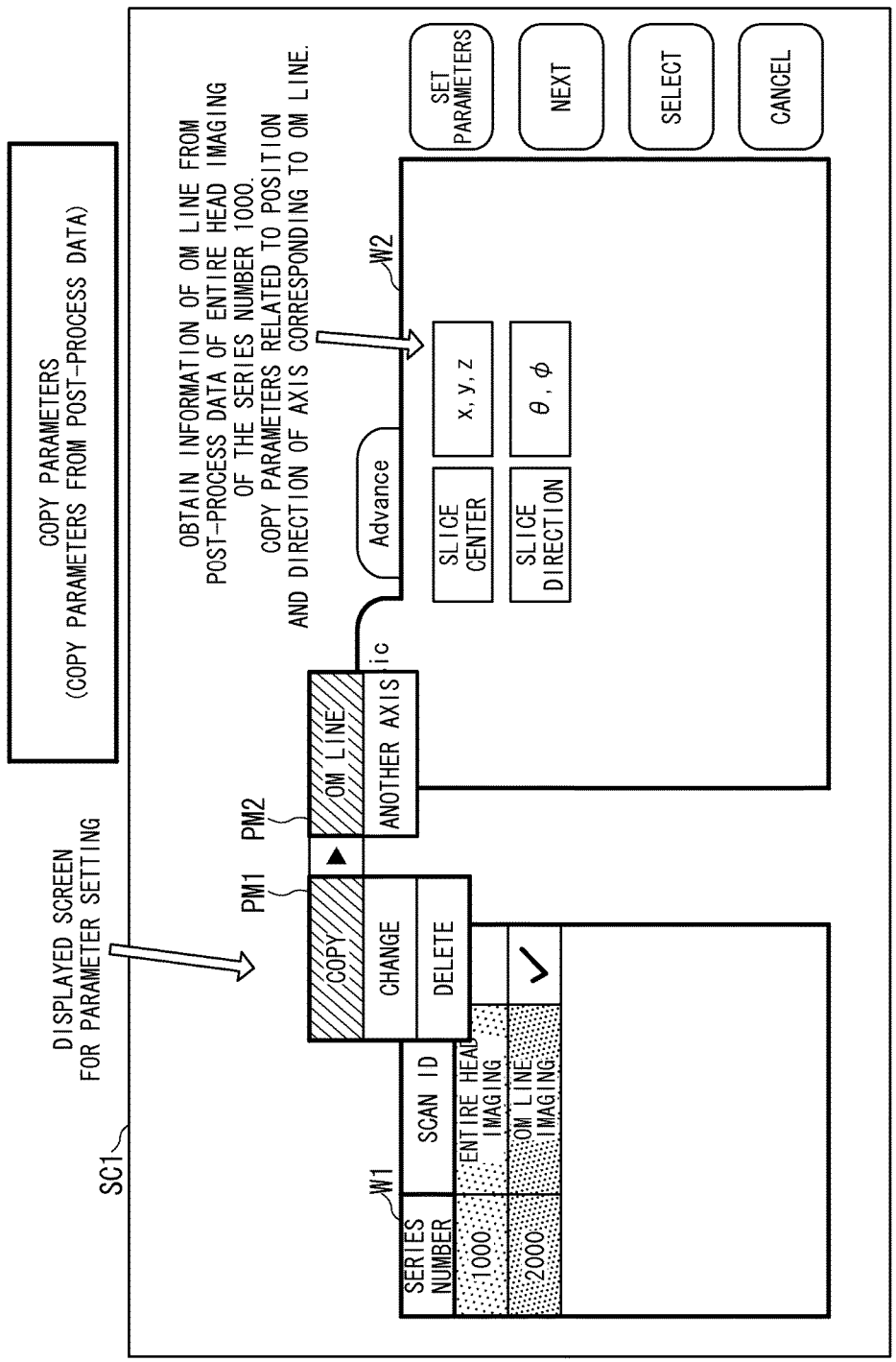
FIG. 12 is a second diagram which illustrates an exemplary operation screen to be used when the parameters are copied and applied from the post-process data.

FIGS. 11 and 12 illustrate another exemplary case of an "OM line imaging study of the head" in which post-process data is copied and applied. The OM line (Orbit Metal line) is a line indicating a section of the head useful for a head diagnosis, and can be obtained by means of a known post-process (position calculation) for a 3D image of the head. According to the embodiment, calculate a position and a direction of a slice corresponding to the OM line obtained by means of a post-process for the entire image of the head taken in the series 1000 (first series), and store the slice position and direction in the parameter storage unit 100 as parameters belonging to an "OM line" group. Then, copy and apply the parameters in the "OM line" group in the parameter storage unit 100 in order to set imaging parameters in the series 2000 (second series) (see FIG. 12). Owing to this function, parameters related to the slice position and direction corresponding to the OM line can be quickly and accurately set.

(3) Case 3: Copy and Apply Parameters Used for Imaging in the Past

In a medical imaging diagnosis, temporal progress of a diseased part is desired to be observed in the same imaging conditions in lots of cases. According to the embodiment, parameters used for imaging in the past can be easily copied and applied as depicted in FIGS. 13 and 14.

Figure 13:
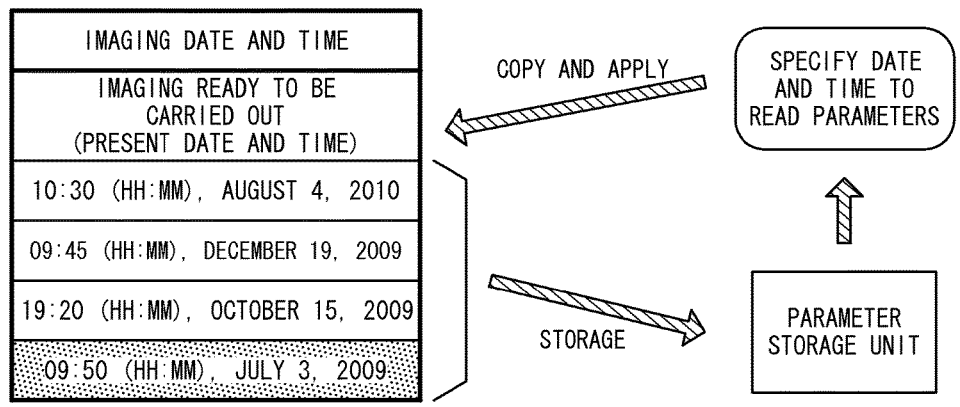
FIG. 13 illustrates an idea of an operation to copy and apply parameters.
Figure 14:
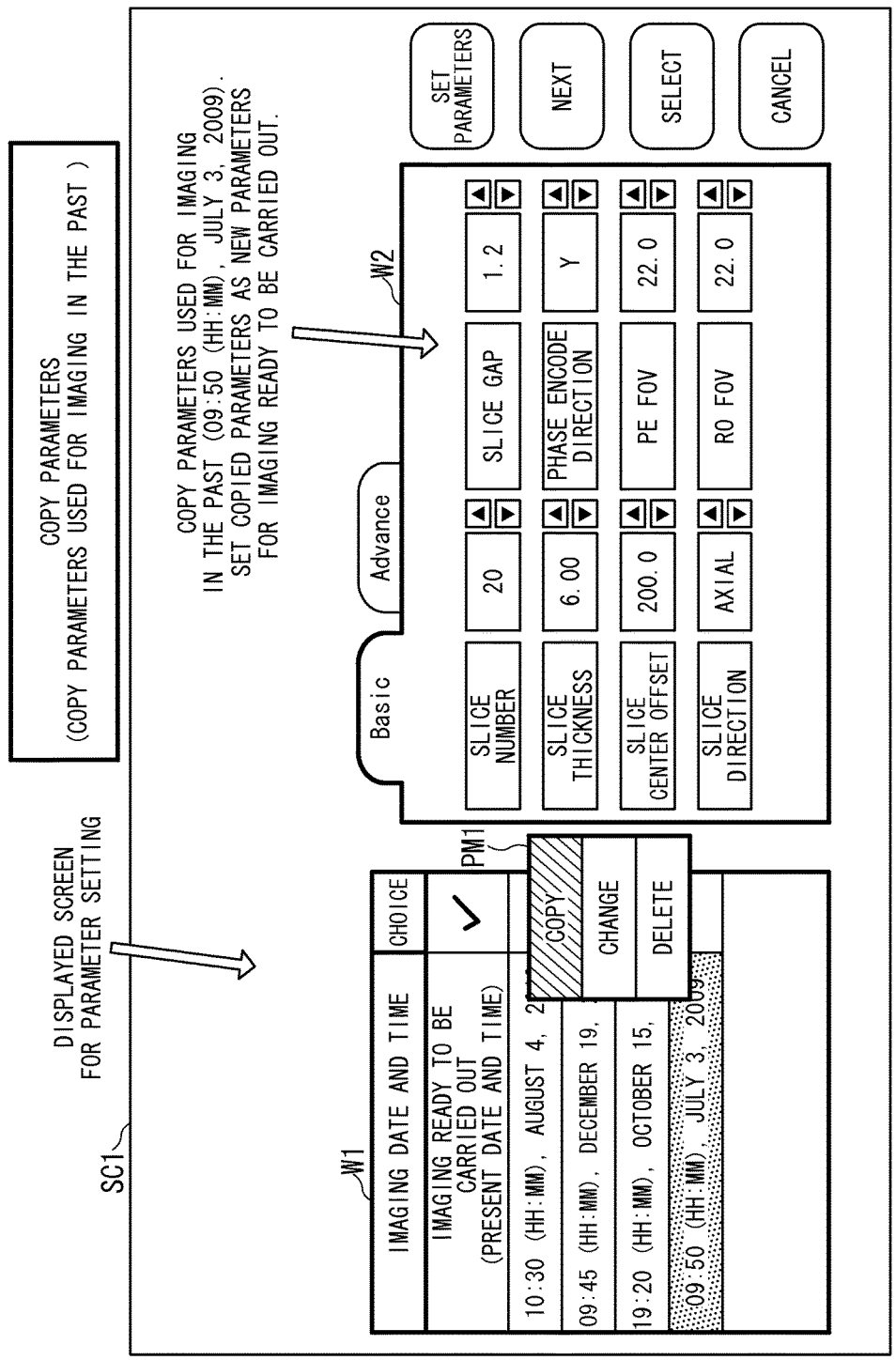
FIG. 14 illustrates an exemplary operation screen to be used when parameters used for imaging in the past are copied and applied.

Specifically, a cluster of parameters used for imaging in the past (the first series of imaging) is grouped according to imaging date and time and stored in the parameter storage unit 100 as depicted in FIG. 13. Then, specify imaging date and time as a group in order to take a new image, so that a set of parameters which was used for imaging at the specified imaging date and time is copied and set as a new set of parameters for imaging (imaging in the second series) as depicted in FIG. 14.

The copy function described above enables same imaging conditions as applied to imaging in the past can be quickly set with high reproducibility.

(4) Case 4: Set Common Parameters Selected According to Scenario

Figure 15:
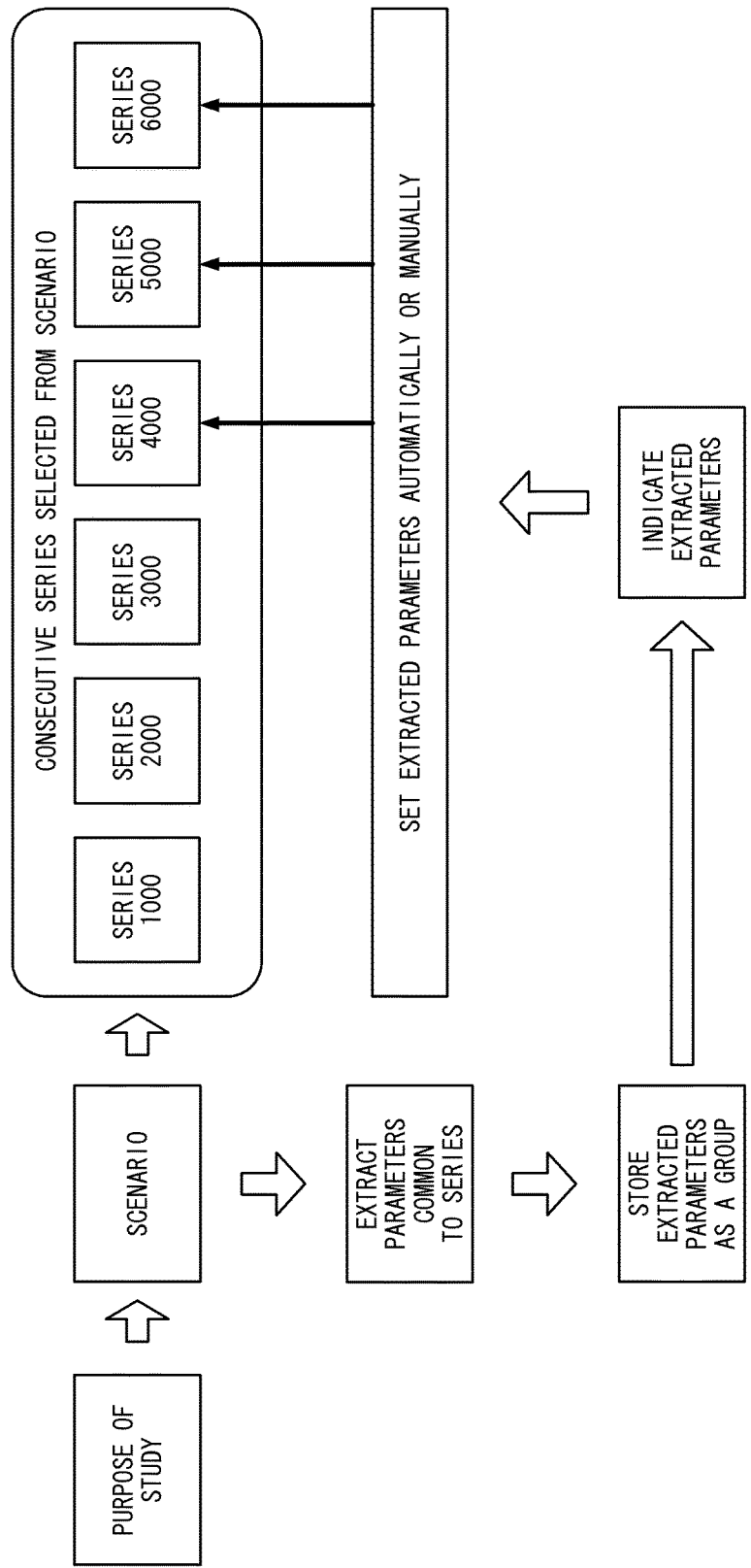
FIG. 15 illustrates an exemplary case in which common parameters selected in accordance with a scenario are set.

FIG. 15 illustrates an example in which common parameters selected in accordance with a scenario are set. In a medical imaging diagnosis such as an MRI imaging diagnosis, a series of imaging is selected usually to a certain extent depending upon a purpose of the study in lots of cases. Such a series of imaging is collectively called a scenario. If the purpose of the study is imaging of the head, e.g., a series of imaging is collectively selected as a scenario as depicted in FIG. 4, in which take an image for positioning and a map image in the series 1000 and 2000, respectively, and carry out three-dimensional TOF imaging so as to take an image of a blood flow in the head in the series 3000. Specify a particular imaging surface (e.g., particular axial surface) and carry out T2- and T1-weighted imaging in the series 4000 and 5000, respectively, and carry out FLAIR imaging on the same imagining surface further in the series 6000. In such a scenario, it is settled as a matter of course that imaging is carried out on one and the same imaging surface of the head with same resolution and different contrast by diagnostic request in lots of cases. Thus, once a scenario is selected in accordance with the purpose of the study, the group of parameters related to the "part" and "resolution" of the imaging surface can be automatically extracted as a group of parameter values to be set for T2-weighted, T1-weighted and FLAIR imaging (series 4000-6000) in common.

According to the exemplary procedure depicted in FIGS. 4-6, e.g., a group of the parameters used in the series 4000 related to the "part" and "resolution" of the imaging surface is separately and manually specified, and the parameter values of the specified group are copied and applied to the series 5000 and 6000. According to the method described above, on the other hand, a group of parameter values to be set in common is automatically extracted so that operation work of a user can be reduced.

The parameter extractor 104 (see FIG. 2) automatically extracts a group of parameter values. The parameter values of the automatically extracted group are indicated on the display unit 64 so as to be checked by the user. After checking the parameter values, the user manually set the parameter values as imaging parameters in the relevant series.

Incidentally, the parameter values of the automatically extracted group can be automatically set as imaging parameters in the relevant series, instead of being manually set by the user. The copy controller 102 sets the parameters.

According to the magnetic resonance imaging apparatus 1 of the embodiment, as described above, parameters for setting various kinds of imaging conditions can be quickly and accurately set without an error by means of the convenient copy function.

Incidentally, the invention is not limited to the embodiment described above as it is, and the components can be modified within the scope of the invention so that the invention is practically embodied. Further, the plural disclosed components of the embodiment can be suitably combined with one another so that various inventions can be formed. Some of the components can be removed, e.g., from all the disclosed components of the embodiment. Further, the components of different embodiments can be suitably combined with one another.

What is claimed is:

1. A magnetic resonance imaging (MRI) apparatus comprising MRI system components configured to carry out plural imaging processes using respectively corresponding sets of imaging conditions for at least one patient image study which produces at least one series of MR images for a patient, the magnetic resonance imaging apparatus comprising at least one processor coupled to memory, a user input port and a user display that have been configured to:
   group a plurality of types of MRI parameters defining some of the plural imaging conditions to be used for carrying out plural imaging processes into a plurality of stored parameter groups;
   cause the user display to display a list of the plural stored parameter groups such that one of the plural stored parameter groups can be designated by a user;
   accept a user-specified designation of a stored parameter group from the displayed list of the plural stored parameter groups to be used as at least a portion of imaging conditions for a first series of imaging processes; and
   copy the user-specified stored parameter group from said first series into imaging conditions to be used for a second series different from the first series,
   wherein the imaging conditions of the first and second series are both used in main scans for generating diagnostic images.

2. The magnetic resonance imaging apparatus according to claim 1, wherein the parameter values belonging to the user-specified group are applied as parameter values for imaging conditions to be used in the second series.

3. The magnetic resonance imaging apparatus according to claim 1, wherein the parameter values belonging to the user-specified group are used for parameter values to be used in the second series.

4. The magnetic resonance imaging apparatus according to claim 1, wherein the grouped types of MRI parameters include a group of parameter values for specifying a part of the patient to be imaged, a group of parameter values for identifying image resolution and a group of parameter values for obtaining different contrast values.

5. The magnetic resonance imaging apparatus according to claim 1, wherein each of the grouped types of MRI parameters is specific to a particular kind of identified MR imaging method.

6. The magnetic resonance imaging apparatus according to claim 1, wherein:
   a same part of a patient is an imaging object both in the first series and in the second series, and
   a parameter value used in the first series of imaging processes is set for identifying a part of the patient to be imaged.

7. The magnetic resonance imaging apparatus according to claim 1, wherein:
   a same resolution value is used both in a first series of imaging processes and in a second series of imaging processes, and
   a parameter value used in the first series of imaging processes is set for identifying a resolution value as a parameter value to be used in the second series of imaging processes for identifying a resolution value on a basis of the groups into which the parameter types are grouped.

8. The magnetic resonance imaging apparatus according to claim 1, wherein:
   two- or three-dimensional position data of the patient is obtained from an image obtained by a post-process of a first series of imaging processes, and
   the two- or three-dimensional position data obtained by the post-process as a parameter value is used for identifying an imaging part in a second series of imaging processes carried out after the first series of imaging.

9. The magnetic resonance imaging apparatus according to claim 1, wherein:
   the magnetic resonance imaging apparatus carries out a plurality of series of imaging processes while changing a plurality of imaging conditions for the patient,
   parameters within a stored parameter group are copied except for a specified particular parameter in that group, and
   parameters used in the first series are set for the second series except for the specified particular parameter.

10. The magnetic resonance imaging apparatus according to claim 1, wherein:
    the magnetic resonance imaging apparatus carries out a second series of imaging processes in a particular period of time after a first series of imaging processes for the same patient,
    a parameter value used in the first series of imaging processes is copied from a group of parameter values identifiable according to relevant imaging date and time, and
    the copied parameter value used in the first series of imaging processes is used as a parameter value in order to carry out the second series of imaging processes.

11. A magnetic resonance imaging (MRI) method for carrying out plural imaging processes for at least one patient image study which produces at least one series of MR images for a patient, the magnetic resonance imaging method comprising:
    using at least one processor coupled to memory, an operator input port and an operator display to effect:
    grouping a plurality of types of MRI parameters defining some of plural imaging conditions to be used for carrying out plural imaging processes providing plural series of images into a plurality of stored parameter groups;
    storing said grouped parameter values corresponding to one of the parameter types on a group basis;
    causing the operator display to display a list of the plural stored parameter groups such that one of the plural stored parameter groups can be designated by an operator;
    accepting an operator-specified group from the displayed list of the plural groups; and
    copying stored parameter values, according to the specified group, the parameter values being copied from imaging conditions used for a first series of images, to imaging conditions to be used for a second series of images different from the first series, wherein the imaging conditions of the first and second series are both used in main scans for generating diagnostic images.

\* \* \* \* \*